United States Patent
Scherninski et al.

(12) 
(10) Patent No.: US 6,192,267 B1
(45) Date of Patent: Feb. 20, 2001

(54) ENDOSCOPIC OR FIBERSCOPIC IMAGING DEVICE USING INFRARED FLUORESCENCE

(76) Inventors: François Scherninski, 5, rue des Goncourt, 75011 Paris; Gabriel Quentel, 2 rue de Gribeauval, 75007 Paris, both of (FR)

(*) Notice: Under 35 U.S.C. 154(b), the term of this patent shall be extended for 0 days.

(21) Appl. No.: 08/704,677
(22) PCT Filed: Mar. 21, 1995
(86) PCT No.: PCT/FR95/00344
§ 371 Date: Nov. 27, 1996
§ 102(e) Date: Nov. 27, 1996

(30) Foreign Application Priority Data

Mar. 21, 1994 (FR) .................................................. 94 03296

(51) Int. Cl.$^7$ ...................................................... A61B 6/00
(52) U.S. Cl. .......................................... 600/473; 600/431
(58) Field of Search .................................. 128/664, 665, 128/654, 656, 633, 634; 600/473, 475, 476, 431, 433, 310, 342, 109, 160

(56) References Cited

U.S. PATENT DOCUMENTS

| | | | |
|---|---|---|---|
| 4,072,147 | * | 2/1978 | Hett . |
| 4,336,809 | * | 6/1982 | Clark ..................................... 128/665 |
| 4,541,438 | * | 9/1985 | Parker et al. .......................... 128/664 |
| 4,556,057 | * | 12/1985 | Hiruma et al. . |
| 4,768,513 | | 9/1988 | Suzuki . |
| 4,919,114 | | 4/1990 | Miyazaki . |
| 4,947,850 | * | 8/1990 | Vanderkooi et al. ................. 128/654 |
| 5,078,150 | * | 1/1992 | Hara et al. ............................ 128/665 |
| 5,104,392 | | 4/1992 | Kittrell et al. . |
| 5,106,387 | | 4/1992 | Kittrell et al. . |
| 5,199,431 | | 4/1993 | Kittrell et al. . |
| 5,215,095 | | 6/1993 | Macvicar et al. . |
| 5,279,298 | | 1/1994 | Flower . |
| 5,290,275 | | 3/1994 | Kittrell et al. . |
| 5,304,173 | | 4/1994 | Kittrell et al. . |
| 5,318,024 | | 6/1994 | Kittrell et al. . |

FOREIGN PATENT DOCUMENTS

| | | | |
|---|---|---|---|
| 32 10 593 | * | 10/1982 | (DE) . |
| 195 375 | | 9/1986 | (EP) . |
| 512 965 | | 11/1992 | (EP) . |
| 554 643 | | 8/1993 | (EP) . |

OTHER PUBLICATIONS

T. Satoh et al. "Use of fluorescent electronic endoscopy in the evaluation of peptic ulcers". Endoscopy 23 (1991), pp. 313–316.

U.K. Franzeck, MD et al. "Dynamic fluorescence video endoscopy for intravital evaluation of gastrointestinal mucosal blood flow". Gastrointestinal Endoscopy. vol. 39, No. 6 (1993), pp. 806–809.

G. Panzardi et al. "Choroidal angiography with indocyanine green dye: absorption and fluorescence techniques". European Journal of Ophthalmology. vol. 2, No. 2 (1992) pp. 83–85.

Hidetoshi Ohta, MD, et al. "The near–infrared electronic endoscope for diagnosis of esophageal varices". Gastrointestinal Endoscopy. vol. 38, No. 3 (1992), pp. 330–335.

* cited by examiner

Primary Examiner—Marvin M. Lateef
Assistant Examiner—Shawna J Shaw
(74) Attorney, Agent, or Firm—Henderson & Sturm LLP

(57) ABSTRACT

An angiography device including an endoscope designed to be inserted into a body cavity, a light source for emitting excitation light in a first wavelength range into the cavity, a digital camera for sensing an image of the body cavity in a second wave range that does not overlap the first wavelength range, and a screen for displaying the sense image, the first and second wavelength ranges lying in the infrared range.

13 Claims, 3 Drawing Sheets

ENDOSCOPIC OR FIBERSCOPIC IMAGING DEVICE USING INFRARED FLUORESCENCE

The invention relates to endoscopic or fiberscopic imaging devices using infrared fluorescence.

More particularly, the present invention relates to an angiography device for inspecting a wall of a body cavity of a patient after the patient has been intravenously injected with a pharmaceutically acceptable fluorescent dye, the dye being capable of emitting light at "fluorescence" wavelengths when excited by light at "excitation" wavelengths, the device comprising:

a flexible duct of small section and having a free end which is designed to be inserted in said body cavity to inspect the wall thereof;

excitation means for emitting "excitation" light from said free end in a first range of wavelengths including at least a portion of the excitation wavelengths of the dye;

reception means for receiving, at said free end, an image of the observed wall in a second wavelength range which includes at least a portion of the fluorescence wavelengths of the dye and which has substantially no overlap with the first wavelength range; and display means for displaying the received image.

Such a device has been disclosed in particular by T. Satoh et al. ("Use of fluorescent electronic endoscopy in evaluation of peptic ulcers", Endoscopy 1991; 23: 313–316) and subsequently by U. K. Franzeck et al. ("Dynamic fluorescence video-endoscopy for intravital evaluation of gastrointestinal mucosa blood flow", Gastrointest. Endosc. 1993; 39; 6: 806–809).

When that type of device is used, a fluorescent dye is injected intravenously into a patient. Under the effect of the excitation light, the dye emits fluoresced light making it possible to observe the vascular network in the wall of the body cavity under examination. Since the great majority of visceral lesions are accompanied by considerable vascular modifications, such lesions can thus be found.

The dye with which the above-mentioned known devices are designed to work is fluorescein which has very good fluorescing efficiency. Because fluorescein is excited by light in the visible range and because it fluoresces likewise in the visible range, the first and second wavelength ranges corresponding to the above-mentioned known devices both lie in the visible light spectrum.

Because visible light is absorbed to a great extent by the tissues forming the wall of the body cavity to be observed, those known devices are therefore capable of observing only the superficial vascular network, which is of little interest, clinically speaking.

Further, fluorescein also has the drawback of diffusing in the interstitial tissue that forms the wall to be observed. This generates background fluorescence that degrades the image.

It is therefore desirable to avoid using fluorescein as the dye, and more generally to avoid using a dye whose excitation and fluorescence wavelengths are situated in the visible range.

Elsewhere, G. Panzardi et al. (EP-A-0 554 643 and "Charoidial angiography with indocyanine green dye: absorption and fluorescence techniques", European Journal of Ophthalmology, Volume 2, No. 2, 1992, pp. 83–85) have disclosed an angiography device enabling the vascular network of a patient's choroid to be observed using indocyanine green as the dye, which has the advantages firstly of making it possible to work in the infrared range, infrared rays being capable of penetrating relatively deeply into tissue, and secondly of not diffusing into tissue outside the vascular network. In addition, indocyanine green is particularly well tolerated by the body.

Unfortunately, indocyanine green fluoresces with very low efficiency, such that the light fluoresced by the wall under observation is likewise of very low level.

Consequently, although the device disclosed by G. Panzardi et al. is suitable for direct observation such as when observing the choroid, it is unsuitable for using fluorescence to observe the wall of a body cavity by means of a fiberscope or an endoscope insofar as a fiberscope gives rise to considerable light attenuation between its inlet and outlet ends, while an endoscope, gives rise to considerable attenuation of excitation light, and a miniature analog camera located at the free end of the endoscope runs the risk of generating considerable background noise because of its miniaturization, thereby degrading the quality of the image and preventing subsequent processing of the image.

An object of the present invention is thus to propose an endoscopic or fiberscopic angiography device using fluorescence that makes it possible to operate in the infrared range, in particular using indocyanine green or any other pharmaceutically acceptable dye that fluorescences in the infrared range, and enabling usable images to be obtained even if the dye used has poor fluorescencing efficiency.

To this end, according to the, invention, a device of the kind in question is essentially characterized in that each of said first and second wavelength ranges lies at least in part in the infrared range, and in that the reception means include a digital sensor for directly transforming the image as sensed into digital signals, and digital processing means for increasing definition, contrast, and brightness in the image as sensed.

Since the excitation light and the fluoresced light both belong to the infrared range, the device of the invention makes it possible to visualize the vascular network of the observed wall in depth.

Also, the image sensed by fluorescence provides an excellent signal/noise ratio because the second wavelength range has substantially no overlap with the first wavelength range, unlike the method of endoscopic angiography by infrared absorption disclosed, in particular, by Hidetoshi Ohta et al. in 1991 ("The near infrared electronic endoscope for diagnosis of esophageal varices", Gastrointest. Endosc., 1992; 38: 330–335).

Because the light signals are transformed immediately into digital signals, this signal/noise ratio is conserved, thereby making it possible to process the image effectively to improve visibility therein.

In preferred embodiments of the invention, use is made of one or more of the following dispositions:

the first wavelength range lies, at least in part, between 766 nm and 815 nm, and the second wavelength range lies, at least in part, between 825 nm and 840 nm;

the excitation means include a high power polychromatic light source, means for sequentially interrupting emission from the light source, an "excitation" optical fiber for conveying the light emitted by the source to the free end of the flexible duct, and an excitation filter disposed to receive all of the light that also passes along the excitation optical fiber, said excitation filter allowing substantially all of the light in the first wavelength range to pass and absorbing substantially all of the light in the second wavelength range;

the means for sequentially interrupting the emission from the light source comprise a mask disposed upstream from the excitation filter;

the light source is a flash lamp;

the light source is of adjustable power;

the excitation filter is removable;

the device includes three color filters each having a separate passband in the visible range, and means for selectively or successively interposing each of said color filters between the light source and the excitation optical fiber;

the excitation means comprise a monochromatic laser source emitting infrared excitation light, and an "excitation" optical fiber for conveying the light emitted by the laser source to the free end of the flexible duct;

the excitation means apply a narrow excitation light beam on the wall to be observed, and include scanning means for moving the excitation light beam so as to cause it to scan the wall to be observed;

the scanning means comprise a mirror pivotable about two mutually perpendicular axes, and control means for controlling pivoting of the mirror about both of said axes, the excitation light beam reaching said mirror and being reflected thereby towards the wall to be observed;

the excitation light beam passes through a fixed semireflecting mirror before reaching the moving mirror, said fixed mirror reflecting, towards a digital detector cell sensitive in the infrared, all light coming from the wall to be observed along a direction travelled by the excitation light beam after it has been reflected on the moving mirror, a stop filter being interposed between the fixed mirror and the detector cell, said stop filter absorbing substantially all light in the first wavelength range and passing substantially all light in the second wavelength range;

the reception means comprise a digital camera responsive in the infrared and connected to the free end of the flexible duct by a reception optical fiber, said reception optical fiber conveying the light it receives at the free end of the flexible duct to the digital camera, a stop filter being disposed so that the light conveyed by the reception optical fiber passes therethrough, said stop filter absorbing substantially all light in the first wavelength range and passing substantially all light in the second wavelength range; and the reception means comprise a digital camera that is sensitive in the infrared and that is disposed inside the flexible duct in the vicinity of the free end thereof, a stop filter being provided at said free end so that all of the light flux received by the digital camera passes therethrough, said stop filter absorbing substantially all light in the first wavelength range and passing substantially all light in the second wavelength range.

Other characteristics and advantages of the invention appear from the following detailed description of four embodiments, given as non-limiting examples, with reference to the accompanying drawings.

In the drawings.

In the figures, the same references designate similar elements.

In the four embodiments of the invention described below, the angiography device includes a flexible duct 1 which may be a fiberscope or an endoscope which extends longitudinally between an end $1_1$ and a free end $1_2$ designed to be inserted into a body cavity 2 of a patient to inspect the wall $2_1$ thereof (see FIG. 1).

The device of the invention is designed to be used after the patient has been intravenously injected with a fluorescent dye that can be excited by infrared radiation to respond by fluorescencing radiation that is likewise in the infrared range, thereby making it possible to observe the vascular network of the observed wall to a relatively great depth from the inside of the body cavity, thus enabling lesions that give rise to vascular modifications to be detected effectively, even if the modifications are very small.

In particular, in the embodiments described below, the device of the invention is specially designed to make it possible to use indocyanine green as the dye, with the absorption and fluorescence spectra thereof being shown respectively by curves 3 and 4 of FIG. 2.

Figure 2:
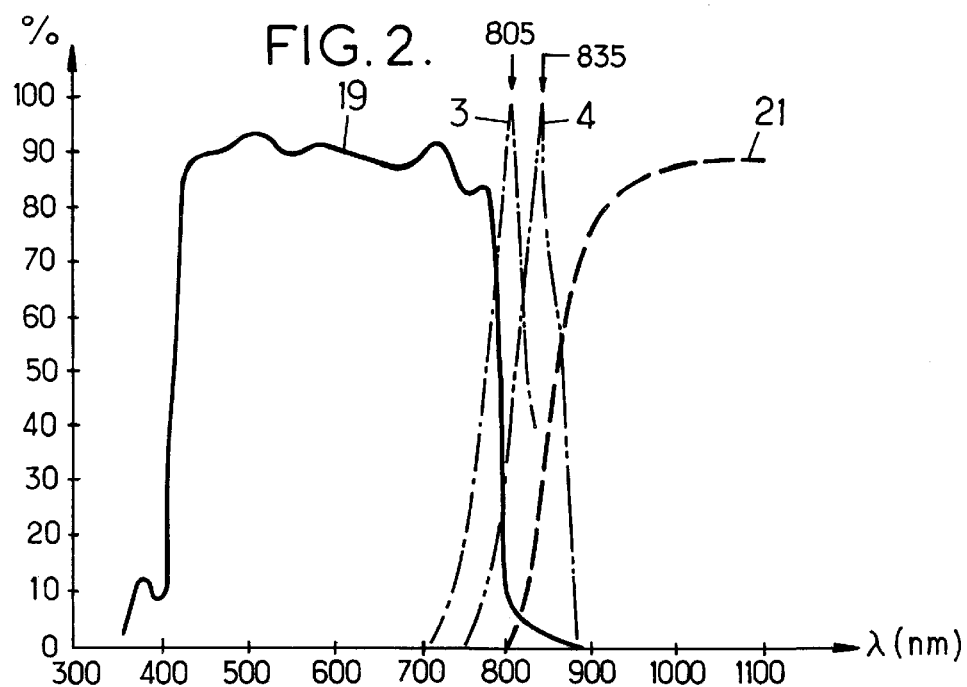
FIG. 2 shows the spectrum transmission curves of the excitation and stop filters of the FIG. 1 device, together with the absorption and fluorescence spectra of indocyanine green.

As can be seen in FIG. 2, the absorption spectrum of indocyanine green has a peak for received radiation having a wavelength of 805 nm, while its fluorescence spectrum has a peak for an emitted wavelength of 835 nm.

The indocyanine green present in the vascular network of the wall $2_1$ is excited by excitation light emitted from the end $1_2$ of the fiberscope or the endoscope, in a first wavelength range including a portion of the infrared spectrum. Preferably, at least a portion of the excitation light must be emitted at wavelengths lying in the range 766 nm to 815 nm so as to excite indocyanine green effectively.

The excitation light causes indocyanine green to emit infrared radiation by the fluorescence phenomenon, with the maximum of the infrared radiation being emitted at a wavelength of 835 nm.

This emission of infrared radiation by fluorescence gives rise to a fluorescencing image of the wall $2_1$ which is received at the free end $1_2$ of the fiberscope or the endoscope. The light signals making up the image are then transformed directly into digital signals, generally electrical signals: this prevents the signal/noise ratio of the light signals as sensed from being deteriorated by any kind of analog processing. As a result, advantage can be taken of the good signal/noise ratio in the light signals constituting the fluorescencing image of the wall $2_1$ in spite of the low luminosity and the low contrast of the image.

In the four embodiments described below, the digital signals coming from the sensor are transmitted to a microcomputer 5 (see FIG. 1) which is connected in conventional manner to a mass storage unit 6 such as an optical disk, to a keyboard 7, to a high definition screen 8, and to a printer 9.

The microcomputer 5 has digital image-processing software to increase definition, contrast, and brightness in the image as sensed.

In particular, the software may:

amplify the received signals;

alter the histogram of gray level distribution in the image so as to improve definition and contrast therein;

transform gray levels in the image into colors; and superpose images.

Because of its image processing performance, the device of the invention makes it possible to use fluorescencing images obtained with indocyanine green as the dye in spite of the low fluorescencing efficiency of that dye and in spite of the attenuation of the light signals that takes place in the endoscope or the fiberscope. In addition, because of its performance, the device of the invention makes it possible to use the dye in small quantities.

When used with indocyanine green, the device of the invention makes it possible to objectify vascular modifications, neovascular structures, and mucous, submucuous, or parenchymal tumors (laparoscopy) at an early stage.

The device of the invention makes it possible to identify lesions soon after indocyanine green has been injected and generally for up to about 30 to 40 minutes after the dye has been injected.

Figure 1:
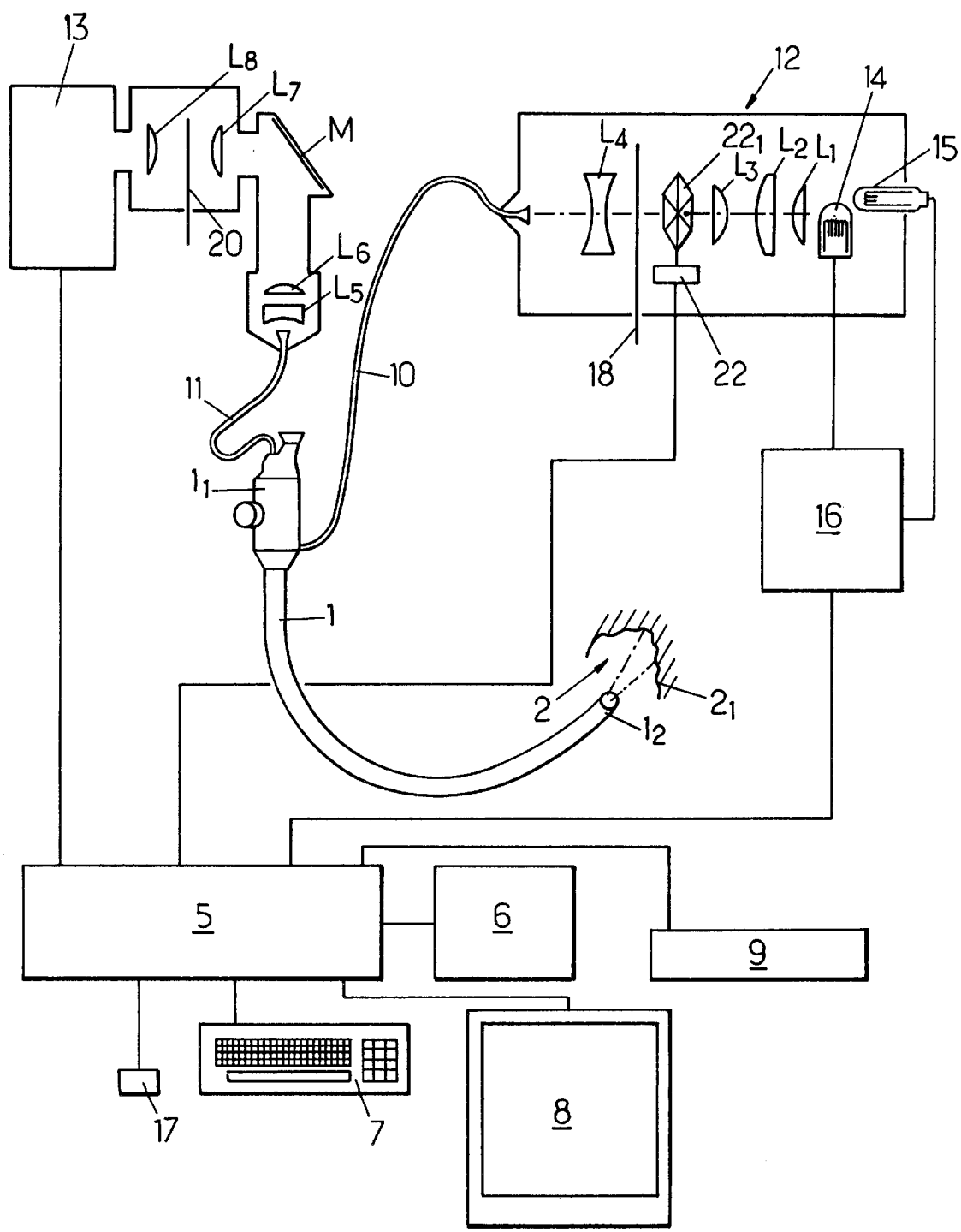
FIG. 1 is a diagrammatic view showing a first embodiment of the invention.

In the first embodiment of the invention shown in FIG. 1, the flexible duct 1 is a fiberscope which contains, in particular, two optical fibers 10 and 11 that are transparent in the infrared, namely an "excitation" optical fiber 10 which conveys the excitation light produced by a light source 12 to the free end $1_2$ of the fiberscope, and a "reception" optical fiber 11 which conveys the image of the observed wall $2_1$ as received at the free end $1_2$ of the fiberscope to a digital camera 13.

The light source 12 comprises firstly a halogen lamp 14 rated at 300 watts or greater, and secondly a xenon flash lamp 15, e.g. delivering 300 watt.s of energy, with both lamps being powered by a dimmer power supply 16 under the control of the microcomputer 5. A trigger 17 connected to the microcomputer 5 serves to trigger flashes from the lamp 15 and takes pictures simultaneously by storing the image at the moment that a flash is emitted by the lamp 15.

The light emitted by the halogen lamp 14 or the flash lamp 15 is applied to the inlet of the excitation optical fiber 10 via various lenses shown diagrammatically at $L_1$, $L_2$, $L_3$, and $L_4$, which lenses are made of glass that is transparent to infrared radiation, preferably a glass that is rich in lead and poor in silica, and of monocubic structure, and via an excitation filter 18 for which one example of a spectrum transmission curve is referenced 19 in FIG. 2.

As can be seen in FIG. 2, the excitation filter 18 allows light to pass substantially in the wavelength range extending from 400 nm to 805 nm, and it absorbs substantially all wavelengths longer than 805 nm. Thus, as can be seen by comparing the curves 3 and 19 of FIG. 2, the excitation filter 18 allows enough infrared light to pass in the excitation wavelengths of indocyanine green to cause the dye to fluorescence sufficiently.

The outlet from the reception optical fiber 11 is connected to the digital camera 13 via an optical system that is likewise transparent to infrared rays (comprising lenses shown diagrammatically at $L_5$, $L_6$, $L_7$, and $L_8$, plus a mirror M), together with a stop filter 20 that stops substantially all of the light in the above-mentioned first wavelength range, while passing substantially all of the light in a second wavelength range corresponding to the wavelengths at which indocyanine green fluoresces, said second wavelength range overlapping the first wavelength range very little or not at all.

An example of the spectrum transmission curve of the stop filter 20 is shown in FIG. 2 under reference 21. By comparing it with the spectrum transmission curve 19, it can be seen that the stop filter 20 passes substantially none of the light transmitted by the excitation filter 18. Also, by comparing the spectrum transmission curve 21 with the fluorescence spectrum 4 of indocyanine green, it can be seen that the stop filter 20 passes a large portion of the light energy emitted by fluorescence by indocyanine green, with the stop filter 20 allowing substantially all light to pass beyond 825 nm.

Thus, the image received by the digital camera is exclusively a fluorescent image, and it is not degraded by the excitation light.

The digital camera 13 is a high resolution camera with good sensitivity in the infrared, e.g. the camera sold by KODAK under trademark "VIDEK MEGA PLUS".

Advantageously, the filters 18 and 20 can be removable so as to enable the device to be used for taking images of the wall $2_1$ in the visible range.

Optionally, only one of the two filters 18 and 20 need be removable, with the non-removable filter being transparent in visible light. The light source also includes a masking device 22 disposed between the excitation filter 18 and the lamp 14 and under the control of the microcomputer 5 to interrupt the emission of excitation light periodically so as to avoid damaging the excitation filter 18, the fiberscope, or the wall $2_1$ while the halogen lamp 14 is being used at high power, in particular during prolonged examination. The masking system 22 may comprise, in particular, a disk $22_1$ that is rotated, having transparent portions and opaque portions that are disposed in succession in front of the inlet of the optical fiber 10. When the excitation light is being periodically interrupted, the software in the microcomputer 5 preferably synchronizes picture taking with periods of illumination.

The disk $22_1$ may optionally be replaced by a disk having a succession of color filters, e.g. blue, yellow, and red. Thus, when working not by fluorescence but in visible light, it is possible to cause the camera 13 to take a succession of monochromatic pictures which can then be combined by the software of the microcomputer 5 by superposition to reconstitute a color image of the wall $2_1$.

Figure 3:
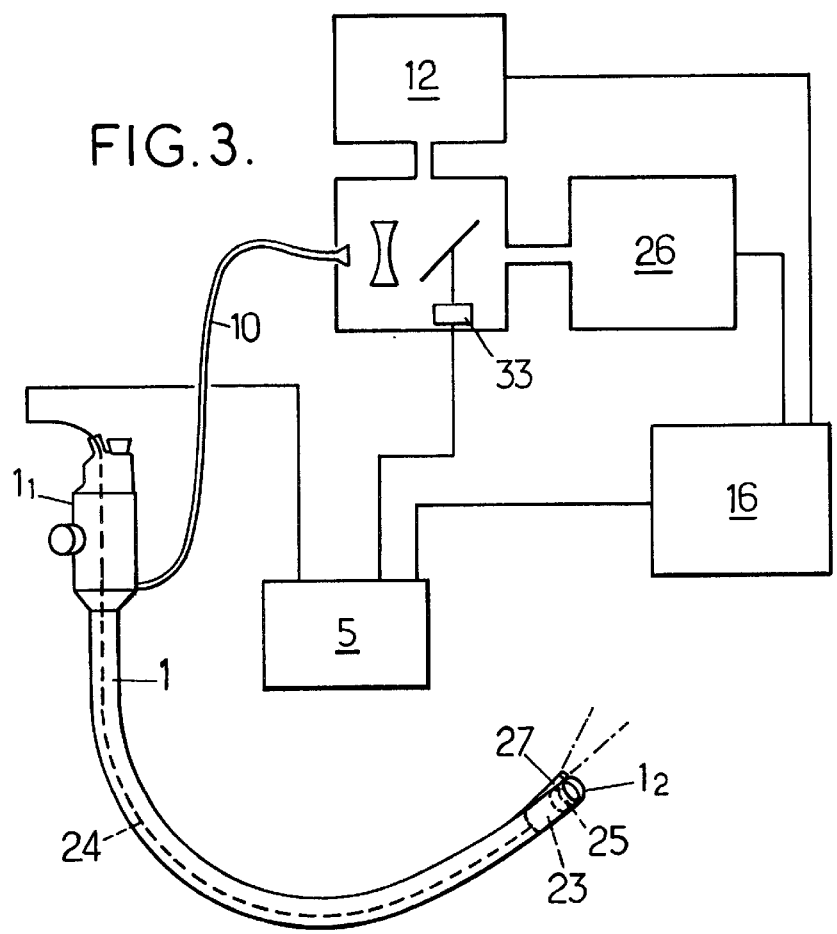
FIG. 3 is a fragmentary diagrammatic view of a second embodiment of the invention.

In the second embodiment of the invention shown in FIG. 3, the flexible duct 1 is an endoscope having, in the vicinity of its free end $1_2$, a miniature digital camera 23 that is sensitive to infrared rays, and a stop filter 25 placed in front of the objective lens of the digital camera 23, the filter passing substantially all wavelengths shorter than 750 nm (the visible range) and longer than 830 nm, while absorbing substantially all light outside those ranges. The camera 23 is connected to the microcomputer 5 by a connection 24.

In this embodiment, the excitation light can be produced by a light source 12 such as that described above; or else it is also possible for the light source 12 to include no excitation filter 18 and to be used solely for viewing the wall when observed in visible light, a monochromatic laser diode 26 being used to produce the excitation light.

In which case, the laser diode emits at a wavelength close to 805 nm, e.g. 793 nm or 815 m, with a narrow bandwidth so as to avoid emitting at a wavelength longer than 825 nm. In this case, it is preferable for the free end $1_2$ of the endoscope to be provided with an optical system 27 connected to the end of the optical fiber 10 to diffuse the monochromatic light towards the wall that is to be observed over an observation angle that is sufficiently large, e.g. 40°.

A pivoting mirror device 33 controlled by the microcomputer 5 enables either the visible light source 12 or the infrared laser diode 26 to be selected.

A sequential interrupter system for the laser diode 26 is preferably provided similar to the device 22 in FIG. 1, but this variance is not shown.

It will be observed that instead of having the filter 25 and the digital camera 23 situated inside the endoscope, the device of FIG. 3 could have a digital camera 13 and a filter 20 located outside the duct and connected to the free end of the duct by a reception optical fiber 11 as described above with reference to FIG. 1 (in which case the duct would again be a fiberscope).

Figure 4:
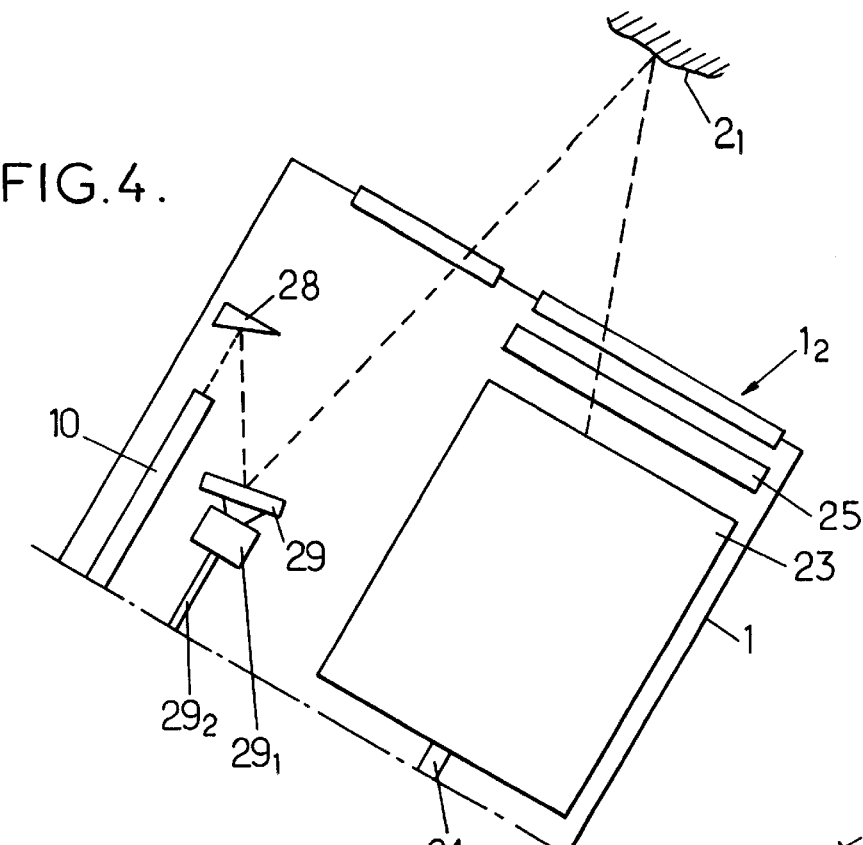
FIG. 4 is a diagrammatic view of the free end of an endoscope in a third embodiment of the invention.

In the embodiment shown in FIG. 4, the flexible duct 1 is still an endoscope, and as in the example of FIG. 3, the excitation light source is a monochromatic laser diode which is connected to the free end $1_1$ of the endoscope by an optical fiber 10.

Unlike the example of FIG. 3, the free end of the endoscope does not include a diffusing optical system 27, but it does include a fixed mirror 28 which reflects the laser beam to a moving mirror 29, and the moving mirror reflects the laser beam to the wall $2_1$ to be observed.

The moving mirror 29 is mounted to pivot about two mutually perpendicular axes, and it is pivoted about these two axes by a device $29_1$ connected to the microcomputer 5 by means of a connection $29_2$ to cause the laser beam to scan the wall $2_1$ to be observed very fast.

The light emitted by fluorescence by the indocyanine green travelling in the vascular network of the wall $2_1$ is then sensed by a digital camera 23 via a stop filter 25. The digital camera 23 and the stop filter 25 are identical or similar to those described in the example of FIG. 3, and as in that example, they are disposed inside the endoscope 1 in the vicinity of its free end, the digital camera 23 being connected to the microcomputer 5 by a line 24.

In this embodiment, the digital camera 23 thus receives the image point by point as the wall $2_1$ is scanned by the laser beam, and the software contained in the microcomputer 5 then reconstitutes the image of the wall $2_1$ after one complete scanning cycle of the laser beam.

Because the light energy of the laser beam is concentrated on a point of the wall $2_1$ at any given instant, the fluorescent response of the indocyanine green is intense, such that the image obtained in this way is of high quality while avoiding any risk of the tissues of the wall $2_1$ being damaged by the laser beam since it scans over the wall.

Figure 5:
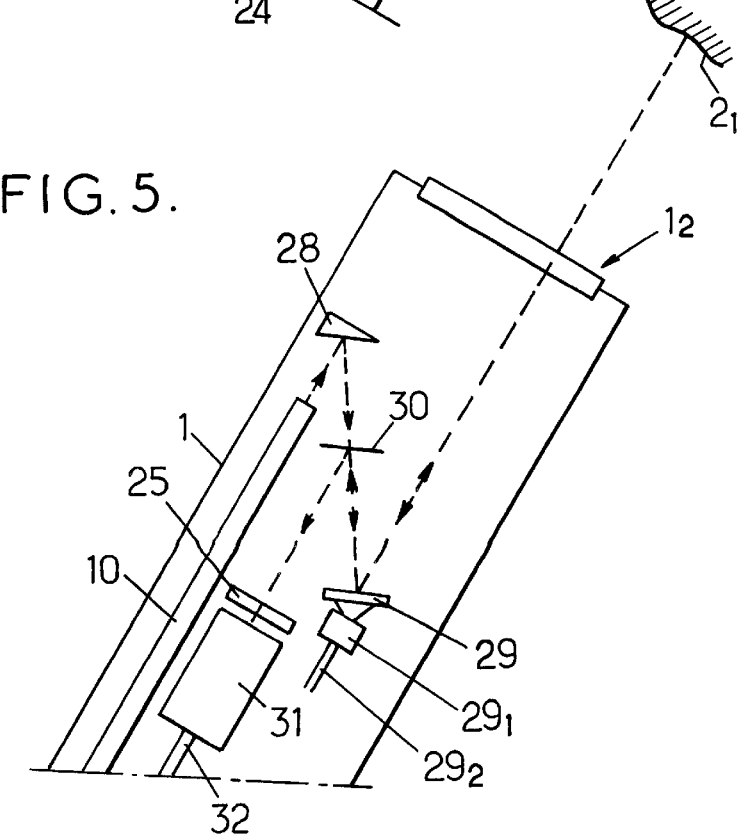
FIG. 5 is a diagrammatic view of the free end of an endoscope in a fourth embodiment of the invention.

The device shown in FIG. 5 operates in similar manner to that of FIG. 4, but it differs therefrom in that it does not include a digital camera 23, but a digital photocell 31 that is responsive in the infrared, which is connected to the microcomputer by a line 32.

A semireflecting fixed mirror 30 is interposed between the fixed mirror 28 and the moving mirror 29 so as to allow the laser beam to pass from the mirror 28 to the mirror 29 while reflecting the light coming from the wall $2_1$ and reflected by the mirror 29 towards the digital cell 31, a stop filter 25 that is identical or similar to the filter 25 of FIG. 4 being interposed between the semireflecting mirror 30 and the digital cell 31.

What is claimed is:

1. An angiography device for inspecting a wall of a body cavity of a patient after the patient has been intravenously injected with a pharmaceutically acceptable dye, the dye being capable of emitting fluorescent light when excited by light having wavelengths which excite the dye, the device comprising:

a flexible duct of small section and having a free end for inserting in a body cavity to inspect a wall thereof;

excitation means for emitting light from said free end in a first range of wavelengths including wavelengths which excite the dye:

reception means for receiving, at said free end, a sensed image of an observed wall in a second wavelength range which includes wavelengths of fluorescent light emitted from the dye and which has substantially no overlap with the first wavelength range; and display means for displaying the received image;

wherein the first wavelength range lies, at least in part, between about 766 nm and about 815 nm, and in which the second wavelength range lies, at least in part, between about 825 nm and about 840 nm; and wherein the reception means comprise a digital sensor for directly transforming the sensed image into digital signals, and digital processing means for increasing definition, contrast, and brightness in the sensed image.

2. A device according to claim 1, in which the excitation means comprise a high power polychromatic light source, means for sequentially interrupting emission from the light source, an optical fiber for conveying the light emitted by the light source to the free end of the flexible duct, and a filter disposed to receive substantially all light that also passes along the optical fiber, said filter allowing substantially all of light in the first wavelength range to pass and absorbing substantially all light in the second wavelength range.

3. A device according to claim 2, wherein the means for sequentially interrupting the emission from the light source comprise a mask disposed upstream from the filter.

4. A device according to claim 2, wherein the light source comprises a flash lamp.

5. A device according to claim 2, wherein the light source comprises an adjustable power light source.

6. A device according to claim 2, wherein the filter comprises a removable filter.

7. A device according to claim 2, comprising at least three color filters, each of said at least three color filters comprising a separate passband in the visible range, and means for selectively or successively interposing each of said at least three color filters between the light source and the optical fiber.

8. A device according to claim 1, wherein the excitation means comprise a monochromatic laser source emitting infrared light, and an optical fiber for conveying the light emitted by the laser source to the free end of the flexible duct.

9. A device according to claim 1, wherein the excitation means comprises means for applying a narrow light beam on the wall to be observed, and comprises scanning means for moving the light beam so as to cause it to scan the wall to be observed.

10. A device according to claim 9, wherein the scanning means comprise a moving mirror pivotable about two mutually perpendicular axes, and control means for controlling pivoting of the mirror about both of said axes, the light beam reaching said mirror and being reflected thereby towards the wall to be observed.

11. A device according to claim 10, wherein the light beam passes through a fixed semi reflecting mirror before reaching the moving mirror, said fixed mirror reflecting, towards a digital detector cell sensitive in the infrared, substantially all light coming from the wall to be observed along a direction travelled by the light beam after it has been reflected on the moving mirror, a stop filter being interposed between the fixed mirror and the detector cell, said stop filter absorbing substantially all light in the first wavelength range and passing substantially all light in the second wavelength range.

12. A device according to claim 1, wherein the reception means comprise a digital camera responsive to infrared wavelengths and connected to the free end of the flexible duct by a reception optical fiber, said reception optical fiber conveying the light it receives at the free end of the flexible duct to the digital camera, a stop filter being disposed so that the light conveyed by the reception optical fiber passes therethrough, said stop filter absorbing substantially all light in the first wavelength range and passing substantially all light in the second wavelength range.

13. A device according claim 1, wherein the reception means comprise a digital camera that is sensitive to infrared wavelengths and that is disposed inside the flexible duct in the vicinity of the free end thereof, a stop filter being provided at said free end so that substantially all light flux received by the digital camera passes therethrough, said stop filter absorbing substantially all light in the first wavelength range and passing substantially all light in the second wavelength range.

* * * * *